United States Patent [19]

Sogli et al.

[11] Patent Number: 5,387,679
[45] Date of Patent: Feb. 7, 1995

[54] PROCESS FOR THE PREPARATION OF CEPHALOSPORINS INTERMEDIATES

[75] Inventors: Loris Sogli, Novara; Daniele Terrassan, Concorezzo; Giuseppe Ribaldone, Gallarate, all of

[73] Assignee: Antibioticos S.p.A., Milan, Italy

[21] Appl. No.: 988,961
[22] PCT Filed: Jul. 14, 1992
[86] PCT No.: PCT/EP92/01595
  § 371 Date: Mar. 15, 1993
  § 102(e) Date: Mar. 15, 1993
[87] PCT Pub. No.: WO93/02085
  PCT Pub. Date: Feb. 4, 1993

[30] Foreign Application Priority Data

Jul. 15, 1991 [GB] United Kingdom ............... 9115287

[51] Int. Cl.6 .................. C07D 501/04; A61K 31/545
[52] U.S. Cl. ........................................ 540/226; 540/227
[58] Field of Search ........................ 540/226, 227, 222

[56] References Cited

U.S. PATENT DOCUMENTS 4,317,907 3/1982 Saikawa et al.
4,385,178 5/1983 Saikawa et al.
4,472,574 9/1984 Hug.

FOREIGN PATENT DOCUMENTS 0065748 12/1982 European Pat. Off.
2379540 9/1978 France.

OTHER PUBLICATIONS

Chemical and Pharmaceutical Bulletin, vol. 33, No. 12, Dec. 1985, Tokyo, Japan, Isamu Saikawa et al.: "An Efficient Method for the preparation of 3-(SUBSTITUTED THIOMETHYL)-7-aminocephalosporins", pp. 5534-5538.

*Primary Examiner*—Nicholas Rizzo
*Attorney, Agent, or Firm*—Oblon, Spivak, McClelland, Maier, & Neustadt

[57] ABSTRACT

The present invention relates to a process for preparing a compound of formula (I)

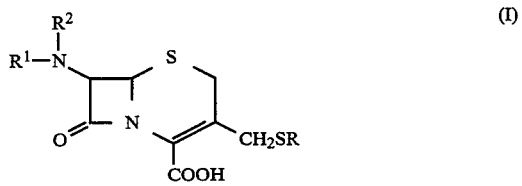

wherein R is an heterocyclic group which contains at least one nitrogen atom with or without oxygen or sulphur and $R^1$ and $R^2$ are both hydrogen atoms or one of them is an hydrogen atom and the other is an acyl group; the process comprising reacting a compound of formula (II)

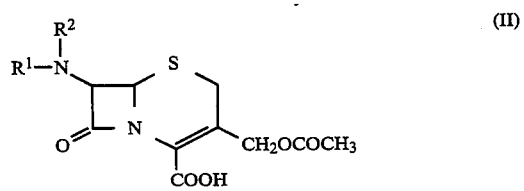

wherein $R^1$ and $R^2$ are each as defined above, and wherein, if necessary, any reactive group is protected by a suitable protective group, or a salt thereof, with a compound of formula (III)

R—SH  (III)

wherein R is as defined above, or a salt thereof, in the presence of an acid and of a compound of formula (IV)

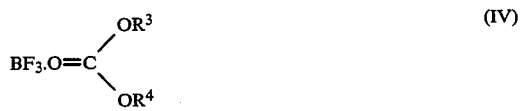

wherein each of $R^3$ and $R^4$ is a $C_1$–$C_4$ alkyl group or $R^3$ and $R^4$ taken together are a $C_2$ or $C_3$ alkylene chain and, if necessary, removing the protective groups possibly present.

The compounds of formula (I) are useful intermediates in the synthesis of Cefazolin and Cefazedone.

13 Claims, No Drawings

PROCESS FOR THE PREPARATION OF CEPHALOSPORINS INTERMEDIATES

The present invention relates to a novel process for preparing derivatives of 7-substituted or unsubstituted aminocephalosporanic acid.

The reaction of a thiol compound with the acetoxy group in 3-position of 7-aminocephalosporanic acid (7-ACA) or a 7-substituted amino derivative thereof is an important reaction in the process to obtain synthetic cephalosporins useful as antibacterial agents.

The 7-amino-3-[(5-methyl-1,3,4-thiadiazol-2-yl)thiomethyl]-cephalosporanic acid, an intermediate of Cefazolin and Cefazedone synthesis, is produced on a large scale reacting 7-ACA with 2-methyl-5-mercapto-1,3,4-thiadiazole in the presence of sodium bicarbonate in aqueous acetone, at pH=6-7.

The yield is very low (about 60%) because of the degradation of the cephem nucleus in these conditions. Other publications, for example L. D. Hatfield, et al., Phil. Trans. R. Soc. London B. 1980, 289, 173, report the reaction of a thiol compound with 7-ACA or its acylderivatives in anhydrous solvents, in the presence of strong acids like methanesulfonic acid, trifluoroacetic acid, boron trifluoride etherate or acetate.

U.S. Pat. No. 4,317,907 discloses, inter alia, a method to produce 7-amino-3-[(5-methyl-1,3,4-thiadiazol-2-yl)thiomethyl]-cephalosporanic acid, reacting 2-methyl-5-mercapto-1,3,4-thiadiazole with 7-aminocephalosporanic acid in acetic acid or nitromethane as solvent, in the presence of boron trifluoride or boron trifluoride etherate with yields of about 86%. The purity of the product obtained by this method is low, 80% max. (see comparative examples a and b) because it contains unreacted 7-ACA and degradation products. The use of an intermediate of low purity affects the yield and the quality of the following step for the production of Cefazolin or Cefazedone.

We have found that the reaction of 7-ACA or 7-substituted aminocephalosporanic acids with a thiol compound proceeds with very high yield when it is effected in dialkyl carbonate, in the presence of a dialkyl carbonate trifluoroborane complex and an aliphatic acid. The product so obtained, can be used without any purification in the following step of the process to produce cephalosporins antibiotics.

A dialkyl carbonate trifluoroborane is a complex of boron trifluoride and a carbonic acid alkyl ester.

The diethyl carbonate trifluoroborane complex has been obtained from boron trifluoride and diethyl carbonate (J. Am. Chem. Soc. 1966, 88, 3058).

The existence of dimethyl carbonate trifluoroborane complex has been demonstrated studying the enthalpy of the complex formation but it has not been isolated. (P. C. Maria et al. J. Phys. Chem. 1985, 89, 1296 and J. Chim. Phys., Phys. Chim. Biol. 1985, 80 (4), 427).

Except the two above reported, no other dialkyl carbonate trifluoroborane complexes are known and they have never been used as catalysts for any reaction.

Another advantage of the invention is the use of dialkyl carbonates as a medium of reaction as far as it concerns environmental hygiene and ecology.

Dialkyl carbonates are, as a matter of fact, substances with a high and greater thermal stability as compared to solvents such as acetonitrile and nitromethane used in the known technique and considered potentially dangerous for the easiness in decomposition.

Dialkyl carbonates have, moreover, a low toxicity, are not mutagenic and they are not therefore dangerous for operators and for the environment.

According to the present invention, there is provided a process for preparing a compound of the formula (I)

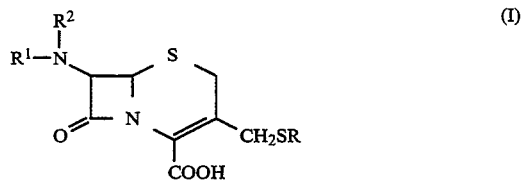

wherein R is an heterocyclic group which contains at least one nitrogen atom with or without oxygen or sulphur and $R^1$ and $R^2$ are both hydrogen atoms or one of them is an hydrogen atom and the other is an acyl group, or a salt thereof; the process comprising reacting a compound of formula (II)

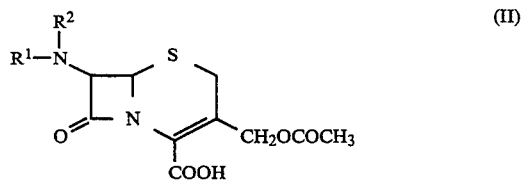

wherein $R^1$ and $R^2$ are each as defined above, and wherein, if necessary, any reactive group is protected by a suitable protective group, or a salt thereof, with a compound of formula (III)

wherein R is as defined above, or a salt thereof, in the presence of an acid and of a compound of formula (IV)

wherein each of $R^3$ and $R^4$ is a $C_1$–$C_4$ alkyl group or $R^3$ and $R^4$ taken together are a $C_2$ or $C_3$ alkylene chain, and, if necessary, removing the protective groups possibly present.

The heterocyclic group R may be, for example, unsubstituted or substituted tetrazolyl, triazolyl, thiadiazolyl, oxadiazolyl or tetrahydrotriazinyl, preferably 1-methyl-1,2,3,4-tetrazol-5-yl, 1-phenyl-1,2,3,4-tetrazol-5-yl, 1-(2-hydroxyethyl)-1,2,3,4-tetrazol-5-yl, 1-(2-aminoethyl)-1,2,3,4-tetrazol-5-yl, 1-carbamoylmethyl-1,2,3,4-tetrazol-5-yl, 1,2,3-triazol-5-yl, 5-methyl-1,3,4-thiadiazol-2-yl, (5-methyl-1,3,4-oxadiazol-2-yl) and 1,2,5,6-tetrahydro-2-methyl-5,6-dioxo-1,2,4,-triazin-3-yl, most preferably 5-methyl-1,3,4-thiadiazol-2-yl.

When $R_1$ is an acyl group is preferably, 5-amino-5-carboxy-1-oxopentyl, aminophenylacetyl, amino-(4-hydroxyphenyl)acetyl, 3,5-dichloro-4-oxo-1 (4H)-pyridinylacetyl, thien-2-yl-acetyl, 1 H-tetrazol-1-yl-acetyl, hydroxyphenylacetyl, (2-amino-thiazol-4-yl) (methoxyimino)acetyl, 2-(2-aminothiazol-4-yl)acetyl, furan-2-yl (methoxyimino)acetyl, phenylsulphoacetyl, most preferably $R^1$ and $R^2$ are both hydrogen atoms.

The preferred dialkyl carbonates trifluoroborane complexes prepared and used according the present invention are:

Dimethyl carbonate trifluoroborane

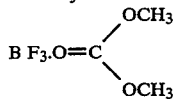

Diethyl carbonate trifluoroborane

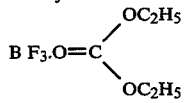

Ethylene carbonate trifluoroborane

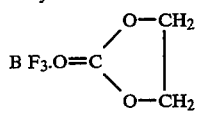

Propylene carbonate trifluoroborane

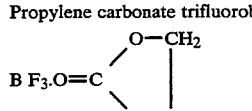

Most preferably, $R^3$ and $R^4$ are methyl.

Suitable protecting groups for the carboxylic group may be, for example, trichloroethyl, benzhydryl, p-nitrobenzyl, p-halophenacyl, pivaloyloxymethyl.

Suitable protecting groups for the amino group may be, for example, phthaloyl,, 2-chloroacetyl, arylmethylene, etc.

The salts of the compounds represented by the general formulae (I) and (II) include both a salt at the acidic group (for example, carboxyl group) and a salt at the basic group (for example, amino group). As the salt at the acidic group, there may be exemplified salts with alkali metals such as sodium, potassium and the like; salts with alkaline earth metals such as calcium, magnesium and the like; ammonium salts, zinc salts, salts with nitrogen-containing organic bases such as triethylamine, diethylamine, pyridine, N-methylpiperidine, N-methylmorpholine, N,N-dimethylaniline and the like. As the salt at the basic group, there may be exemplified salts with mineral acids, such us hydrochloric acid, sulfuric acid and the like; salts with organic acids such as oxalic acid, formic acid, trichloroacetic acid, trifluoroacetic acid and the like; and salts with sulfonic acids, such as methanesulfonic acid, toluenesulfonic acid, naphthalenesulfonic acid and the like. These salts may be previously prepared and isolated or may be prepared in the reaction system.

Salts of the thiol compound represented by the general formula (III) may be in the basic salt form or in the acidic salt form depending upon the type of R and include both the basic and acidic salts above.

The reaction between the compound of formula (II) and the compound of formula (III) may be carried out, e.g., in a solid-liquid phase in a solvent at a temperature of from about 0° C. to about 40° C. for a period of from about 30 minutes to about 6 hours, preferably at a temperature of about 35° C. for a period of about 30 minutes to about 2 hours.

Preferably the solvent is a compound of formula (V)

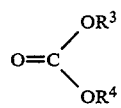

wherein $R^3$ and $R^4$ are as defined above. In particular, dimethyl carbonate, diethyl carbonate, ethylene carbonate or propylene carbonate are the preferred solvents, dimethyl carbonate is the most preferred.

Preferably the acid is an aliphatic organic acid, preferably formic acid or acetic acid and it is present in a concentration of about 5% to about 20% of the solvent weight. The compounds of formula (II), (III) and (V), are known.

The compounds of formula (IV), as defined above, may be prepared absorbing boron trifluoride in a compound of formula (V), as defined above, at a temperature from about 0° C. to about 40° C. until the complex of formula (IV) precipitates. The complex is filtered and dried under vacuum.

Alternatively, the compound of formula (IV), as defined above may be prepared "in situ" by adding boron trifluoride to a suspension containing a compound of formula (II), a compound of formula (III) and an acid as defined above, using as solvent a compound of formula (V) as defined above.

The possible removal of the protecting groups may be carried out by known methods, following known procedures.

The invention will be more readily understood from the following operating examples, which are submitted as illustrations only, and not by way of limitation.

EXAMPLE 1

43 g of boron trifluoride were passed into 200 ml of dimethyl carbonate under stirring at 25°–30° C. for 20 minutes. The resulting crystalline precipitate was filtered in dry nitrogen atmosphere, washed with pentane and dried under vacuum at room temperature to constant weight to give 98 g of dimethyl carbonate trifluoroborane, as white crystals.

Elementary analysis values ($C_3H_6O_3.BF_3$): Calcd. (%) C: 22.8; H 3.8; F 36.1 Found (%) C: 21.4; H 4.0; F 34.7

EXAMPLE 2

135 g of dimethyl carbonate trifluoroborane, as obtained in Example 1, were added portionwise in 1 hour to a stirred suspension of 40 g of 7-aminocephalosporanic acid (95% HPLC pure, 0.1398 mol) and 19.6 g of 2-methyl-5-mercapto-1,3,4-thiadiazole in 130 ml of dimethyl carbonate containing 20 g of 99% formic acid, mantaining the temperature at 20° C.

After the addition was complete, the obtained solution was stirred for further 1 hour at 20° C., cooled to 0° C. and diluted with 320 ml of water under cooling.

The pH was adjusted to 0.5 with 15% sodium hydroxide solution and after stirring at 0°–5° C. for 60 minutes, the resulting precipitate was filtered, washed with 200 ml of water and 200 ml of acetone and thereafter dried under vacuum at 40° C. to give 46.7 g of 7-amino-3-[(5-methyl-1,3,4-thiadiazol-2-yl)-thiomethyl]-cephalosporanic acid having a purity of 93% by HPLC (90.3% yield).

EXAMPLE 3

175.5 g of diethyl carbonate trifluoroborane, obtained according the preparation described in J.A.C.S. 1966, 88, 3058, were added portionwise during a period of 90 minutes to a stirred suspension of 40 g of 7-aminocephalosporanic acid (95% HPLC pure, 0.1396 mol) and 19.6 g of 2-methyl-5-mercapto-1,3,4-thiadiazole in 90 ml of diethyl carbonate containing 60 ml of glacial acetic acid, maintaining the temperature at 30°–35° C.

The resulting solution was stirred for about 2 hours at 30°–35° C. and treated as described in Example 2 to give 44.7 g of 7-amino-3-[(5-methyl-1,3,4-thiadiazol-2-yl)-thiomethyl]-cephalosporanic acid having a purity of 91% by HPLC (84.6% yield).

EXAMPLE 4

To a stirred suspension of 40 g of 7-aminocephalosporanic acid (95% HPLC pure, 0.1396 mol) and 19.6 g of 2-methyl-5-mercapto-1,3,4-thiadiazole in 200 ml of dimethyl carbonate containing 35 ml of glacial acetic acid were added 57 g of boron trifluoride in 50 minutes at 30°–35° C.

The resulting solution was stirred for 90 minutes at 20°–25° C. and treated as described in Example 2 to give 45.2 g of 7-amino-3-[(5-methyl-1,3,4-thiadiazol-2-yl)-thiomethyl]-cephalosporanic acid with a purity of 92% by HPLC (86.5% yield).

EXAMPLE 5

To a stirred suspension of 40 g of 7-aminocephalosporanic acid (95% HPLC pure, 0.1396 mol) and 19.6 g of 2-methyl-5-mercapto-1,3,4-thiadiazole in 230 ml of glacial acetic acid were added 57 g of boron trifluoride in 60 minutes at 30°–35° C.

The resulting solution was stirred at 30°–35° C. for 90 minutes and treated as described in Example 2 to give 37.3 g of 7-amino-3-[(5-methyl-1,3,4-thiadiazol-2-yl)-thiomethyl]-cephalosporanic acid. HPLC analysis showed a 88.3% purity and a 6.6% content of unreacted 7-aminocephalosporanic acid (68.5% yield).

EXAMPLE 6

21 g of boron trifluoride were passed into 100 ml of acetonitrile and to this solution were added 14.5 g of 7-aminocephalosporanic acid (95% HPLC pure, 0.0506 mol) and 8.5 g of 2-methyl-5-mercapto-1,3,4-thiadiazole.

The mixture was stirred for 45 minutes at 30° C.

The resulting solution was treated as described in Example 2 to give 7.4 g of 7-amino-3-[(5-methyl-1,3,4-thiadiazol-2-yl)-thiomethyl]-cephalosporanic acid with a purity of 85.9% by HPLC (36.4% yield).

EXAMPLE 7

28 g of boron trifluoride were passed into 50 ml of dimethyl carbonate containing 35 ml of glacial acetic acid.

The solution was added to a stirred suspension of 20 g of 7-aminocephalosporanic acid (95% HPLC pure, 0.0698 mol) and 9.8 g of 2-methyl-5-mercapto-1,3,4-thiadiazole in 50 ml of dimethyl carbonate. The mixture was stirred for 90 minutes at 35° C.

The resulting solution was treated as described in Example 2 to give 21.9 g of 7-amino-3-[(5 methyl-1,3,4-thiadiazol-2-yl)-thiomethyl]-cephalosporanic acid with a purity of 93.3% by HPLC (85.0% yield).

EXAMPLE 8

28.9 g of boron trifluoride were passed during a period of 50 minutes into a stirred suspension of 20 9 of 7-aminocephalosporanic acid (95% HPLC pure, 0.0898 mol, and 9.8 g of 2-methyl-5-mercapto-1,3,4-thiadiazole in 132 g of ethylene carbonate and 17.5 ml of glacial acetic acid, maintaining the temperature at 35° C.

The mixture was kept at 35° C. per 30 minutes under stirring. The resulting solution was treated as described in Example 2 to give 21.4 g of 7-amino-3-[(5-methyl-1,3,4-thiadiazol-2-yl)-thiomethyl]-cephalosporanic acid with a purity of 93.9% by HPLC (83.6% yield).

EXAMPLE 9

61 g of boron trifluoride were passed during a period of 1 hour into a stirred suspension of 40 g of 7-aminocephalosporanic acid (95% HPLC pure, 0.1396 mol) and 19.8 g of 2-methyl-5-mercapto-1,3,4-thiadiazole in 200 g of propylene carbonate containing 35 ml of glacial acetic acid, maintaining the temperature at 20° C.

The mixture was kept at 20° C. per 80 minutes under stirring. The resulting solution was treated as described in Example 2 to give 43.8 g of 7-amino-3-[(5-methyl-1,3,4-thiadiazol-2-yl)-thiomethyl]-cephalosporanic acid with a purity of 94.7% by HPLC (86.3% yield).

EXAMPLE 10

40.7 g of boron trifluoride were passed into a solution of 100 ml of dimethyl carbonate and 25 ml of formic acid under stirring at 20° C. for 30 minutes.

The resulting solution was added to a stirred suspension of 47.3 g of 7-aminocephalosporanic acid (95% HPLC pure, 0.165 mol) and 23.3 g of 1-methyl-5-mercapto-1,2,3,4-tetrazole in 150 ml of dimethyl carbonate.

The mixture was maintained at 45° C. for 90 minutes, cooled at 20° C., treated with 50 ml of 20% HCl and stirred at 5° C. for 90 minutes.

The precipitate thereby formed was collected by filtration, washed with 150 ml of dimethyl carbonate and suspended in 230 ml of acetone at 5° C. After addition of a mixture of 400 ml of water and 150 ml of acetone, the slurry was adjusted to pH 2.7 with 32% ammonium hydroxide and stirred for 30 minutes. The solid was filtered, washed with 100 ml of water and 150 ml of acetone and thereafter dried under vacuum at 40° C. to give 49.8 g of 7-amino-3-[(1-methyl-1,2,3,4-tetrazol-5-yl)-thiomethyl]-cephalosporanic acid having a purity of 97% by HPLC (89.0% yield).

EXAMPLE 11

To a stirred suspension of 50 g of 7-aminocephalosporanic acid (95% HPLC pure, 0.1745 mol) and 22.8 g of 5-mercapto-1,2,3-triazole sodium salt in 300 ml of dimethyl carbonate containing 16 ml of formic acid were added 70 g of boron trifluoride in 15 minutes at 20°–25° C. The mixture was kept at 30°–35° C. for 3 hours under stirring, cooled to 5° C. and added to 300 ml of chilled water.

The pH was adjusted to 1.4 with 20% ammonium hydroxide and the resulting precipitate was filtered, washed with water and dissolved in sodium bicarbonate solution to a final pH 7.5–8. The solution was stirred at 20° C. for 15 minutes in the presence of decolorizing carbon, filtered and acidified with 10% hydrochloric acid to a final pH 4.0.

The slurry was stirred at 20° C. for 1 hour, filtered, washed with water and acetone and thereafter dried under vacuum at 40° C. to give 31 g of 7-amino-3-[(1,2,3-triazol-5-yl)-thiomethyl]-cephalosporanic acid having a purity of 90% by HPLC (51% yield).

EXAMPLE 12

24 g of boron trifluoride were passed into a solution of 100 ml of dimethyl carbonate and 5 ml of formic acid under stirring at 20° C. for 30 minutes.

After addition of 13.4 g of 2,5-dihydro-6-hydroxy-2-methyl-3-mercapto-5-oxo-1,2,4-triazine and 24 g of 7-aminocephalosporanic acid (95% HPLC pure, 0.08376 mol), the mixture was stirred at 25° C. for 20 minutes, cooled at 20° C. and poured into 100 ml of chilled water.

The pH was adjusted to 1.7 with 15% ammonium hydroxide and after stirring for 15 minutes the resulting precipitate was filtered, washed with water, acetonitrile and acetone, and vacuum dried at 40° C. to give 27 g of 7-amino-3-[(2,5-dihydro-6-hydroxy-2-methyl-5-oxo-1,2,4-triazin-3-yl)-thiomethyl]-cephalosporanic acid having a purity of 93.0% by HPLC (80.7% yield).

COMPARATIVE EXAMPLE a (1) In 81 ml of acetic acid were suspended 8.2 g of 7-aminocephalosporanic acid (95% HPLC pure, 0.0286 mol) and 4 g of 2-methyl-5-mercapto-1,3,4-thiadiazole, and 28.9 g of boron trifluoride diethyl ether complex was added to the resulting suspension to convert the suspension to a solution.

This solution was heated at 55° C. for 30 minutes. After the completion of the reaction the solvent was removed by distillation under reduced pressure and to the residue were added 48 ml of acetone and 48 ml of $H_2O$.

The resulting solution was cooled with ice and the pH was adjusted to 4.0 with 28% ammonia water.

The crystals thus precipitated were collected by filtration, washed with 15 ml of water and 15 ml of acetone and thereafter dried to give 8.6 g of 7-amino-3-[(5-methyl-1,3,4-thiadiazol-2-yl)-thiomethyl]-cephalosporanic acid. HPLC analysis showed a 80.4% purity and a 10.5% content of unreacted 7-aminocephalosporanic acid (70.2 yield).

Because of the high content of unreacted 7-aminocephalosporanic acid, the obtained product is not utilizable as intermediate in the following step for the production of Cefazolin or Cefazedone.

(2) Following the procedures described in the preceding Example (1), but increasing the reaction time from 30 minutes to 60 minutes, 7.4 g of 7-amino-3-[(5-methyl-1,3,4-thiadiazol-2-yl)-thiomethyl]-cephalosporanic acid with a purity of 90.3% were obtained (67.8% yield).

(3) Following the procedures described in the preceding Example (1), but using 30 g of boron trifluoride diethyl ether complex, 8.7 g of 7-amino-3-[(5-methyl-1,3,4-thiadiazol-2-yl)-thiomethyl]-cephalosporanic acid with a purity of 81.3% were obtained (71.8% yield).

COMPARATIVE EXAMPLE b

In 140 ml of nitromethane were suspended 27.2 g of 7-aminocephalosporanic acid (95% HPLC pure, 0.0949 mol) and 13.3 g of 2-methyl-5-mercapto-1,3,4-thiadiazole, and 35 g of boron trifluoride were added to the resulting suspension at a temperature of 0° to 5° C.

This solution was subjected to reaction at room temperature for two hours.

The kinetics of the reaction was controlled.

The concentrations of the reagent and the product (mg/ml) at various times are reported herebelow:

|  | 45 min. | 75 min. | 120 min. |
|---|---|---|---|
| 7-aminocephalosporanic acid | 7.1 | 3.9 | 1.2 |
| 7-amino-3-[5-methyl-1,3,4-thiadiazol-2-yl)-thiomethyl]-cephalosporanic acid | 19.5 | 8.9 | 5.4 |

After 2 hours, the solution was cooled and diluted with 150 ml of water, after which the pH of the solution was adjusted to 4.0 with 28% ammonia water with ice-cooling.

The precipitated was a colored viscous product, without any value.

We claim:

1. A process for preparing a compound of formula (I)

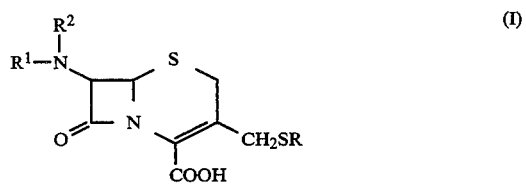

wherein R is an heterocyclic group which contains at least one nitrogen atom with or without oxygen or sulphur and $R^1$ and $R^2$ are both hydrogen atoms or one of them is an hydrogen atom and the other is an acyl group; the process comprising reacting a compound of formula (II)

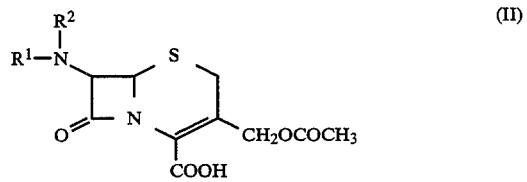

wherein $R^1$ and $R^2$ are each as defined above, and wherein, if necessary, any reactive group is protected by a suitable protective group, or a salt thereof, with a compound of formula (III)

R—SH     (III)

wherein R is as defined above, or a salt thereof, in the presence of an acid and of a compound of formula (IV)

wherein each of $R^3$ and $R^4$ is a $C_1$–$C_4$ alkyl group or $R^3$ and $R^4$ taken together are a $C_2$ or $C_3$ alkylene chain and, if necessary, removing the protective groups possibly present.

2. A process according to claim 1 wherein R is unsubstituted or substituted tetrazolyl, triazolyl, thiadiazolyl, oxadiazolyl or tetrahydrotriazinyl and each of $R^3$ and $R^4$ is methyl or ethyl or $R^3$ and $R^4$ taken together are an ethylene or propylene chain.

3. A process according to claim 1 wherein R is 1-methyl-1,2,3,4-tetrazol-5-yl, 1-phenyl-1,2,3,4-tetrazol-5-yl, 1-(2-hydroxyethyl)-1,2,3,4-tetrazol-5-yl, 1-(2-aminoethyl)-1,2,3,4-tetrazol-5-yl, 1-carbamoylmethyl-1,2,3,4-tetrazol-5-yl, 1,2,3-triazol-5-yl, 5-methyl-1,3,4-thiadiazol-2-yl, 5-methyl-1,3,4-oxadiazol-2-yl or 1,2,5,6-tetrahydro-2-methyl-5,6-dioxo-1,2,4-triazin-3-yl; $R^1$ is hydrogen and $R^2$ is hydrogen, 5-amino-5-carboxy-1-oxopentyl, aminophenylacetyl, amino-(4-hydroxyphenyl)acetyl, 3,5-dichloro-4-oxo-1 (4H)-pyridinylacetyl, thien-2-yl-acetyl, 1H-tetrazol-1-yl-acetyl, hydroxy phenylacetyl, (2-amino-thiazol-4-yl)(methoxyimino)acetyl, 2-(2-aminothiazol-4-yl)acetyl, furan-2-yl(methoxyimino)acetyl or phenylsulphoacetyl and $R^3$ and $R^4$ are methyl or ethyl $R^3$ and $R^4$ taken together are ethylene or propylene.

4. A process according to claim 3 wherein R is 5-methyl-1,3,4-thiadiazol-2-yl, $R^1$ and $R^2$ are hydrogen atoms and $R^3$ and $R^4$ are methyl.

5. A process according to any one of claims 1 to 4 wherein the reaction is carried out in a solid-liquid phase in a solvent at a temperature of from about 0° C. to about 40° C. for a period of from about 30 minutes to about 6 hours.

6. A process according to claim 5 wherein the solvent is a compound of the formula (V)

wherein $R^3$ and $R^4$ are as defined in claim 1.

7. A process according to claim 6 wherein the compound of formula V is dimethyl carbonate, diethyl carbonate, ethylene carbonate or propylene carbonate.

8. A process according to claim 7 wherein the compound of formula V is dimethyl carbonate.

9. A process according to any one of the preceding claims wherein the acid is an aliphatic carboxylic acid.

10. A process according to claim 9, wherein the acid is formic or acetic acid and is present in a concentration of about 5% to about 20% of the solvent weight.

11. A process according to any one of the preceding claims wherein the reaction is carried out at a temperature of about 35° C. for a period of about 30 minutes to about 2 hours.

12. A process according to any one of the preceding claims wherein the compound of formula (IV) is prepared "in situ" by adding boron trifluoride to a suspension containing the compound of formula (II), the compound of formula (III) and the acid using, as solvent, a compound of formula (V) as defined in claim 6.

13. A process for the preparation of Cefazolin or Cefazedone, which process comprises converting into Cefazolin or Cefazedone 7-amino-3-[(5-methyl-1,3,4-thiadiazol-2-yl)thiomethyl]-cephalosporanic acid which has been prepared by a process as claimed in any one of the preceding claims.

* * * * *

UNITED STATES PATENT AND TRADEMARK OFFICE
CERTIFICATE OF CORRECTION

PATENT NO. : 5,387,679
DATED : February 7, 1995
INVENTOR(S) : Loris SOGLI, et al.

It is certified that error appears in the above-indentified patent and that said Letters Patent is hereby corrected as shown below:

On the title page, Item [75], the inventorship should read:

--Loris Sogli, Novara; Daniele Terrassan, Concorezzo; Giuseppe Ribaldone, Gallarate, all of Italy.--

Signed and Sealed this

Second Day of May, 1995

BRUCE LEHMAN

*Attest:*

*Attesting Officer*  *Commissioner of Patents and Trademarks*